United States Patent [19]

Puskas et al.

[11] 3,953,475

[45] Apr. 27, 1976

[54] POLYBUTENE COMPOSITION CONTAINING HALO-CARBONYL ADDITIVES

[75] Inventors: Imre Puskas, Glen Ellyn; John A. Cengel, Wheaton, both of Ill.

[73] Assignee: Standard Oil Company, Chicago, Ill.

[22] Filed: May 10, 1973

[21] Appl. No.: 358,958

[52] U.S. Cl. ............................ 260/346.8 R; 526/74; 526/208
[51] Int. Cl.² ........................................ C07D 307/60
[58] Field of Search ................. 260/346.8 R, 346.8, 260/78.4

[56] References Cited
UNITED STATES PATENTS 3,018,250   1/1962   Anderson et al............ 260/346.8 R Primary Examiner—Harry I. Moatz
Attorney, Agent, or Firm—Fred R. Ahlers; Arthur G. Gilkes; William T. McClain

[57] ABSTRACT

Viscous polybutenes of number average molecular weight ($\overline{M}_n$) in the range of about 300 to 3000 have improved reactivity with intramolecular anhydrides of unsaturated aliphatic dicarboxylic acids when reacted in the presence of rather small amounts, i.e., 5 to 200 ppm, of alpha halogen-containing, preferably chlorine or bromine-containing, aliphatic or aromatic carbonyls including acetals as additives. Use of such halogen-containing additives in the addition reaction of polybutene with said unsaturated anhydrides can reduce formation of undesired tarry product resulting from polymerization and/or thermal decomposition of the unsaturated anhydrides.

4 Claims, No Drawings

POLYBUTENE COMPOSITION CONTAINING HALO-CARBONYL ADDITIVES

BACKGROUND OF INVENTION

Viscous polybutenes of about 300 to about 3000 $\overline{M}_n$ have viscosities in the range of about 4 to about 5500 centistokes at 100°C. Such polybutenes are commercially available from polymerization of refinery butenes: isobutylene, cis-butene-2 and butene-1 generally present with butane in a $C_4$ fraction. Commercially since about 1940, such $C_4$ fraction with or without added isobutylene, isobutylene rich concentrates has been polymerized in the presence of Friedel-Crafts catalyst. The wide range in viscosity and molecular weight depends, as is known, on polymerization temperature, to a lesser extent on catalyst and its concentration, and on the olefin content of the feed. The viscous polybutenes are essentially water white and thermally decompose with no residue at temperatures above 275°C. and have some use applications in engine oils and anti-scuff agents and viscosity index improvers and in fuels for internal combustion engines to reduce or suppress deposits in the fuel induction system.

The viscous polybutenes have also found use as components of caulking compounds, adhesives and electric-cable insulating oils. However, the greatest use of the viscous polybutenes is as a raw material in the manufacture of addition agents for fuels and gasoline because the viscous polybutenes are reactive olefins and provide branched-chain alkyl structure in derivatives enhancing their solubility in petroleum products such as lubricant oils, fuels and refinery streams. The derivatives of most interest in the past 15 years are from the polybutenyl-substituted intra-molecular anhydrides of aliphatic dicarboxylic acids such as succinic anhydride. The polybutenyl-substituted saturated aliphatic anhydrides have been used per se, or as diesters, amides, imides, amidines, imidines, and neutral or overbased basic metal salts as addition agents in petroleum products. The addition agents from polybutenes of $\overline{M}_n$ below 500 are mainly used in fuels; for example in gasoline to inhibit rusting, carburetor deposits, and carburetor icing and in diesel fuels to inhibit rust, corrosion and smoke, and in motor oils and industrial oils as rust and wear inhibitors.

The addition agents from polybutenes of 500 to about 3000 $\overline{M}_n$ have found extensive use as detergent-dispersants in motor oils and lesser use as carburetor detergents in gasoline, heat exchanger antifoulants in refinery streams, rust and corrosion inhibitors in surface coatings and as emulsifiers and demulsifiers.

The viscous polybutenes are complex mixtures of polymers, copolymers and interpolymers of isobutylene, cis-butene-2 and butene-1. The nature and relative amounts of the butene monomers involved in the polymerization leading to a particular $\overline{M}_n$ polybutene are not indicative of the resulting polymer product because extensive isomerization occurs during polymerization. The viscous polybutenes, although largely mono-olefins, may contain 0 to 20% isoparaffins. The unsaturation in the viscous polybutene molecules is predominantly in a terminal or near terminal group which, as later illustrated, are of the trisubstituted or vinylidene type. The non-olefinic chain portion of the polybutene molecules is composed of normal butyl and isobutyl units and hence is a long and branched alkyl chain. Such long, branched alkyl chain of the lighter (below 500 $\overline{M}_n$) polybutenes contain relatively greater amounts of normal butyl units and lesser amounts of iso-butyl units. The heavier (500–3000 $\overline{M}_n$) polybutenes contain relatively greater amounts of isobutyl units and lesser amounts of normal butyl units which are concentrated near the end of the long, branched alkyl chain. For example, the structures of a polydisperse polybutene of about 900 $\overline{M}_n$ have in part been identified through the use of infrared spectroscopy (calibrated by NMR) and permanganate cleavage. The principal structures identified are shown below (in decreasing order of concentration):

(I)

(II)

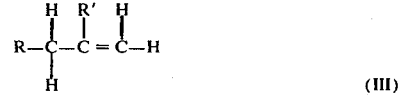
(III)

wherein R is the long, branched alkyl chain and comprises about 60 mole % $(C_4)_{4 \text{ to } 11}$, about 30 mole % $(C_4)_{12 \text{ to } 35}$ and about 10 mole % $(C_4) > 35$; R' is mainly methyl but is also ethyl; and the ratio of iso-$C_4$ to n-$C_4$ is about 3:1.

With respect to polybutene addition reactivity with unsaturated intramolecular anhydrides, it is believed, that the olefinic terminal groups in the three structures shown above are in the decreasing reactivity order of III, I and II. In the uncatalyzed addition reaction some of the slower reacting molecular species remain unreacted and with the isoparaffinic polymer species (0–20 percent of the total polymer product) which do not react at all, the desired polybutenyl-substituted saturated anhydride product can be obtained in yields of 75–80 percent based on starting polymer.

Such addition reaction between the viscous polybutene and intramolecular anhydride of unsaturated aliphatic dicarboxylic acid can typically use any one of maleic anhydride, citraconic anhydride, itaconic anhydride, ethyl maleic anhydride, halo (e.g., chloro-) maleic anhydride, glutaconic anhydride, homomesaconic anhydride, and the like according to U.S. Pat. Nos. 2,628,942 and 2,634,256 among others. The addition reactions are, in general, conducted at temperatures in the range of 150° to 300°C using polybutene to anhydride molar ratios of reactants in the range of 1.0:1.0–15, generally 1.0:1.05–1.15. In addition to the nonreaction of some olefinic species of polybutene and isoparaffinic entities thereof amounting to a total of up to 40–50 percent of the polybutene charged, there is also a problem with respect to thermal decomposition and polymerization of the unsaturated anhydride reactant at temperatures upward from 150°C.

Thermal decomposition at temperatures upward from 150°C. of unsaturated aliphatic dicarboxylic acids and their anhydrides (e.g. maleic and its anhydride) has been known and is reported, for example in U.S. Pat. No. 3,476,774 which gives earlier documentation sources therefor. Such thermal decomposition is accompanied by evolution of water vapor and oxides of carbon, in a closed reaction vessel, is accompanied by an increase in internal pressure. Under some observed conditions the thermal decomposition can be so substantially instantaneous as to be explosive. In the absence of explosive thermal decomposition a carbon-containing residue is also formed in addition to water vapor and oxides of carbon. Such thermal decomposition and attendant polymerization of the unsaturated anhydride reactant has been observed as occurring during its addition reaction with polymeric olefins, e.g. polybutenes and others, in a closed reaction vessel. There is the increase of internal pressure by involved water vapor and oxides of carbon (mainly $CO_2$) but the attendant carboncontaining residue varies in nature from somewhat granular when the decomposition is only slight to a tarry material mainly adhering to internal surfaces of the reaction vessel when the decomposition is more extensive but well below explosive magnitude. The granular type residue amounts to from about 0.1 to about 0.3 weight percent of the total charge, in general, is dispersed in the product, the alkenyl-substituted saturated anhydride addition compound diluted with unreacted components of the olefin polymer, is readily separated therefrom by filtration. However, the tarry residual product, which for the most part fouls the internals of the reaction vessel can be as high as 2–3 weight percent of the total charge. The tarry residual material not adhering to reactor internals fouls the filter and interferes with filtration of the desired reaction product. Both types of residue are undesirable because of the above noted fouling characteristics and because their formation results in yield reduction of the desired alkenyl-substituted anhydride addition product.

Various means have been proposed and/or used to suppress thermal conversion of unsaturated anhydride reactant. German Pat. No. 1,102,142 for its reaction of triene (e.g., 1,5,9-cyclododecatriene) with maleic anhydride to prepare a 1:1 addition product teaches the use of from 0.01 to 5 weight percent of thionine, phenothiazine, hydroquinone, and related inhibitors. U.S. Pat. No. 3,231,587 teaches the use of chlorine gas in molar amounts equal to maleic anhydride for its addition reaction with olefin polymers (the resulting alkenylsuccinic anhydride contains 0.4–0.5 weight percent chlorine) as a superior to earlier proposed first preparing a chlorinated olefinic polymer having 4–15 weight percent chlorine and reacting the chloropolymer with maleic anhydride. U.S. Pat. No. 3,476,774 teaches the use of a hindered phenol nonreactive with the olefin polymer or maleic anhydride (e.g. 2,6-ditertbutylphenol or 4,4'-methylenebis-2,6-ditertbutylphenol) to suppress thermal decomposition.

Such hindered phenols are not readily removed from the adduct product. The chloro-substituted adduct may not be useful in all cases for the preparation of addition agent derivatives.

In our laboratories the use of small, i.e., catalytic amounts of hydrogen chloride during the adduct formation between olefinic polymer and maleic anhydride achieved success in improving yield and reducing formation of undesired tarry material. A drawback of this method is the possible corrosive nature of the stored product. However, it is understood, that hydrogen halides can react with the olefinic polymer forming alkyl halides. It is also recognized, that at higher temperatures, due to decomposition of the alkyl halides, hydrogen halide and halogen formation are possible. Hence it is recognized, that addition of trace quantities of hydrogen halide or halogen or alkyl halides to the polymer could achieve the desired improvement in the addition reaction. It was also recognized, that the effectiveness of such halo-compounds will vary with process conditions and exact chemical nature and concentration of the added material.

From the standpoint of both the manufacturer-merchant of the viscous polybutenes and the purchasers-users thereof it would be desirable to modify such polybutene compositions by addition of a small amount of material which enhances reactivity of the polybutene and suppresses formation of the undesirable tarry material without undesirable added effects. It would be further desirable that such modification of the polybutenes be accomplished by a simple, single process step of not only combining a small amount of material with the polybutene to effect the desired reactivity enhancement and tarry material suppression but also by use of a material which is readily removable from the adduct reaction product. For this latter benefit it is pointed out that unreacted anhydride, including that used in slight molar excess per mole of polybutene, is removed from the adduct reaction product by evaporation at an absolute pressure in the range of 5 to 760 mm Hg. and at a temperature below reaction temperature. Thus it is beneficial to add to the polybutene such material having the above-beneficial effects on the adduct reaction and at the same time readily removable at said temperature and pressure conditions at which unreacted unsaturated anhydride is removed.

SUMMARY OF INVENTION

It has now been discovered that viscous polybutenes of from about 300 to about 3000 $\overline{M}_n$ containing 10 to 200, preferably from 5 to 200 ppm on weight basis of halogen, more suitably chlorine and/or bromine, containing aliphatic or aromatic ketones or acetals provides a novel, uniquely modified polybutene composition. Such polybutene composition can be reacted at temperatures of 150°–300°C. with unsaturated anhydride without effecting chemical substitution of either the reactants or the adduct product, the halo-additive can be removed from the adduct product under conditions of removing unreacted unsaturated-anhydride, enhances polybutene conversion to adduct, and suppresses tarry material formation.

To be most readily removable with unreacted unsaturated anhydride at 10 to 760 mm Hg., the halo-hydrocarbon added to viscous polybutene should have sufficient vapor pressure at such pressures to facilitate their removal. Preferred as chloro- or bromo- aliphatic or aromatic ketones acetals are those having a normal (atmospheric pressure) boiling point up to 225°C. but it can be as low as 40°C.

Typical, but not all inclusive, of such chlorinated and/or brominated aliphatic or aromatic ketones and acetals are:

A. The halo-ketones typically are alpha-chloro or -bromo ketones and di(alpha-chloro- or bromo) ketones. The former include mono, di- and tri-alpha chloro- or bromo-acetone; mono- and di-alpha chloro- or bromo-methylethylketone, diethylketone, methylpropyl ketone, ethylpropylketone, ethylisopropylketone, diisopropylketone, di-n-propylketone methyl n-butylketone, ethylisobutylketone, methyl tert. butylketone, n-butylisopropylketone, n-propylisobutylketone, n-propyl tert. butylketone, di-n-butylketone, diisobutylketone, etc. of the symmetrical and mixed alkyl ketones having in addition to the keto carbonyl carbon up to a total of twenty carbon atoms. The alpha-chloro- or bromo-alkyl diketones are those having two keto-carbonyl carbons in a chain of carbon atoms which are otherwise alkyl as in a chain of 4 to 22 carbon atoms wherein the chlorine or bromine atom or atoms is attached to a chain carbon adjacent to a keto carbonyl carbon. Such alpha chloro- or bromo-diketones are illustrated by 1,4-dichloro or dibromo-2,3-butanedione; 1,5-dichloro or dibromo-3,3-dimethyl-2,4-pentanedione; 2,6-dichloro or dibromo-4,4-dimethyl-3,5-hexanedione; 2,6-dichloro or dibromo-4,4-dimethyl-3,5-heptanedione; 1,4-dichloro- or dibromo-2,3-pentanedione; 2,5-dichloro- or dibromo-3,4-hexanedione, and the like. The alpha-chloro- or bromo aromatic ketones are preferably mixed alkyl aryl ketones with the chlorine or bromine on the alpha alkyl carbon as in alpha-chloro or alpha-bromoacetophenone, alpha-chloro- or alpha-bromoacetonaphthone, and the like.

B. The alpha-chloro or alpha-bromo acetals are preferably $C_1$-$C_{10}$ dialkyl acetals of alpha-chloro- or alpha-bromo- acetaldehyde because the acetaldehyde acetals are more available than acetals of other aldehydes. Of such preferred alpha-chloro or alpha-bromoacetaldehyde diethyl acetals are most preferred.

The reaction between the viscous polybutenes and the anhydrides of unsaturated aliphatic dicarboxylic acids known to the art to be useful for the addition reaction producing alkenyl-substituted saturated anhydride, is conducted commercially in a batchwise or continuous manner in a stirred-tank type autoclave or equivalent reaction vessel providing intimate contact between the reactants. For batchwise operation the reactants are charged to the closed reaction vessel with or without displacing its air with oxygenfree, e.g. nitrogen, atmosphere at ambient pressure. The reactants can be at ambient temperature but the polybutene reactant is usually at an elevated temperature to reduce the time for the reaction mixture to reach reaction temperature. Solid anhydride reactant can be charged alone or dispersed in the polybutene or alone as a melt. The reaction mixture is stirred while being heated to reaction temperature and during reaction.

Continuous conduct of the addition reaction is maintained by charging to the reaction vessel containing the stirred adduct forming reaction mixture a melt of the anhydride reactant and preheated viscous polybutene so that their combined heat supplies the heat input needed during reaction.

Reaction time for batchwise operation is, in general, 4–8 hours. Continuous operation requires, in general, a shorter residence time, for example 1–3 hours.

Thermal decomposition of anhydride reactant, which evolves $CO_2$ and water vapor, causes an undesirable pressure increase as well as formation of undesirable tarry material during the adduct reaction. Such pressure increase, although undesirable, can be used as an indicator of failure to suppress formation of such tarry material by the additive of the polybutene composition. The actual extent of formation of such tarry material is, of course, determined gravimetrically after termination of the addition reaction and removal of unreacted anhydride reactant at the before mentioned pressure in the range of 5 to 760 mm Hg.

The manner and nature of enhanced adduct yield by the alpha-halo ketone or acetal additive is not understood. We speculate that isomerization of the olefin double bond to a more reactive species is accomplished under the effect of trace decomposition products derived from the alpha-chloro- or alpha-bromo ketone or acetal. Further, such trace impurities can also act as radical quenchers and inhibit the decomposition or polymerization of unsaturated anhydride to tar.

The present inventive use of the alpha-chloro or alpha-bromo- ketones or acetals and the benefits to be derived therefrom in addition reactions with the before mentioned unsaturated anhydride will now be illustrated using maleic anhydride, the most commonly, commercially used of those anhydride reactants. These examples were conducted in small reactivity screening tests using a 22 ml volume Parr bomb having a magnetic stirrer. In each illustrative example 10.0 grams of polybutene and about 1.1 grams of powdered maleic anhydride (MA) to provide a polymer: MA mole ratio of 1.0:1.1 were charged. The air was displaced from the bomb with nitrogen, the bomb scaled and immersed in a 249° oil bath, the reaction mixture stirred for six hours, and then sampled.

A weight aliquot portion of each reaction product so produced was chromotographed on silica gel column. The unreacted polybutene was eluted from the column with hexane and determined gravimetrically to allow the calculation of the weight percent of polybutene that reacted with MA. The total tarry product produced was also determined gravimetrically and calculated as weight percent of the total charge (polymer +MA).

TABLE

EFFECT OF ALPHA-Cl OR Br KETONE OR ACETAL ON ADDUCT AND TAR

| Example Number | Additive Name | Concentration, ppm Additive | Cl | Br | Adduct Yield, % | Tar, Wt. % |
|---|---|---|---|---|---|---|
| 1 | None | 0 | 0 | 0 | 63.3 | 1.3 |
| 2 | 1,4-Dibromo-2,3-butanedione | 73 | 0 | 48 | 75.5 | 0.2 |
| 3 | alpha-Bromoacetonaphthone | 63 | 0 | 20 | 73.0 | 0.4 |
| 4 | Chloro-acetaldehyde diethyl acetal | 150 | 35 | 0 | 64.8 | 1.4 |
| 5 | alpha-Bromoacetophenone | 76 | 0 | 30 | 72.3 | 0.2 |
| 6 | alpha-Chloracetophenone | 151 | 35 | 0 | 62.6 | 1.3 |

The alpha brominated additives were superior both with respect to adduct yield improvement and tar suppression as compared to alpha- chlorinated additives when used in the same magnitude of halogen concentration.

While the foregoing examples illustrate benefits afforded by present inventive polybutene compositions containing viscous polybutenes having $\overline{M}_N$ of 900–950, the use of other viscous polybutenes in the $\overline{M}_n$ range of about 300 to 3000 will provide polybutene compositions affording yield improvement and suppression of tarry material in the manner and nature above illustrated for the maleic anhydride reactions illustrated. Similar benefits can be expected by the use of the present inventive polybutene compositions with other of the before named unsaturated anhydrides of aliphatic dicarboxylic acids. Furthermore, the use of the more active alpha- bromo ketone or acetal additives can futher, according to this invention, be extended to reaction of the unsaturated anhydrides with other 300–3000 $\overline{M}_n$ olefinic reactants (e.g., polypropenes).

Finally, the alpha-bromo ketone or acetal additives are equally useful whether they are added to the 300–3000 $\overline{M}_n$ olefin reactant, the unsaturated anhydride or mixtures thereof.

What is claimed is:

1. A method of preparing polybutenylsuccinic anhydride which comprises reacting at a temperature in the range of 150°–300°C in the proportions of from 1.0 to 1.5 moles maleic anhydride per mole of 300–3000 $\overline{M}_n$ polybutene in the composition comprising said polybutene and based on the weight thereof as additive from 5 to 200 ppm of an alpha-bromo dialkyl ketone having in addition to the keto-carbonyl carbon atom up to a total of twenty carbon atoms, alpha-dibromo-substituted alkyl diketone wherein its two keto-carbonyl carbon atoms are in a chain of from 4 to 22 carbon atoms and each bromo- substituent is on a chain carbon atom adjacent to a keto-carbonyl carbon atom, or alpha-bromo aceto-phenone or napthone, or $C_1$–$C_{10}$ dialkyl acetal of alpha-bromo acetaldehyde which additive has a normal boiling point in the range of from 40°C up to 225°C.

2. The method of claim 1 wherein the additive is 1,4-dibromo-2,3-butanedione.

3. The method of claim 1 wherein the additive is alpha-bromoacetonaphthone.

4. The method of claim 1 wherein the additive is alpha-bromoacetophenone.

* * * * *